United States Patent
Murphy et al.

[11] Patent Number: 6,117,695
[45] Date of Patent: Sep. 12, 2000

[54] APPARATUS AND METHOD FOR TESTING A FLIP CHIP INTEGRATED CIRCUIT PACKAGE ADHESIVE LAYER

[75] Inventors: Adrian S. Murphy; Manickam Thavarajah; Patrick J. Variot, all of San Jose, Calif.

[73] Assignee: LSI Logic Corporation, Milpitas, Calif.

[21] Appl. No.: 09/075,300

[22] Filed: May 8, 1998

[51] Int. Cl.[7] .................................................. H01L 21/44
[52] U.S. Cl. ............................... 438/15; 438/108; 73/827
[58] Field of Search ........................... 73/827, 856, 760, 73/781; 438/15, 106, 107, 108, 118, 119, 121, 122, 125

[56] References Cited

U.S. PATENT DOCUMENTS

| | | | |
|---|---|---|---|
| 3,634,930 | 1/1972 | Cranston | 438/15 |
| 5,164,037 | 11/1992 | Iwami et al. | 156/584 |
| 5,313,841 | 5/1994 | Layher | 73/827 |
| 5,337,614 | 8/1994 | Jiang et al. | 73/827 |

*Primary Examiner*—Carl Whitehead, Jr.
*Assistant Examiner*—Jeff Vockrodt
*Attorney, Agent, or Firm*—B. Noel Kivlin; Conley Rose & Tayon

[57] ABSTRACT

An apparatus and method are presented for testing an adhesive layer formed between an integrated circuit and a plate, wherein the plate may be semiconductor device package substrate or a heat spreader. The apparatus includes a pull stud and a pull arm. The pull stud has an upper portion and a lower portion, wherein the lower portion is attached to a surface of the integrated circuit opposite the plate. The upper portion of the pull stud may be, for example, a tapered cylinder having a large end and a small end. The small end meets the lower portion of the pull stud. The pull arm has two opposed ends and at least one bracket for receiving a force. One of the pull arm ends has a "V"-shaped opening surrounded by a lip which receives the upper portion of the pull stud. During use, the lip contacts and retains the upper portion of the pull stud. The opening has an upper wall, and an upper surface of the pull stud contacts the upper wall when the upper portion of the pull stud is inserted into the opening. The lip is vertically displaced from the upper wall such that the lip contacts the upper portion of the pull stud a spaced distance from where the upper surface of the pull stud contacts the upper wall of the opening. In this way, the pull stud and the pull arm are substantially mechanically locked together during use of the apparatus.

3 Claims, 8 Drawing Sheets

APPARATUS AND METHOD FOR TESTING A FLIP CHIP INTEGRATED CIRCUIT PACKAGE ADHESIVE LAYER

BACKGROUND OF THE INVENTION

1. Field of Invention

This invention relates to integrated circuit packages, and more particularly to the testing of the mechanical properties of various adhesive layers used to connect members of a flip chip integrated circuit package.

2. Description of Related Art

During manufacture of an integrated circuit (e.g., a microprocessor), signal lines formed upon the silicon substrate which are to be connected to external devices are terminated at flat metal contact regions called input/output (I/O) pads. Following manufacture, the integrated circuit (i.e., chip) is typically secured within a protective semiconductor device package. Each I/O pad of the integrated circuit is then connected to one or more terminals of the device package. The terminals of a device package are typically arranged about the periphery of the package. Fine metal wires are typically used to connect the I/O pads of the integrated circuit to the terminals of the device package. Some types of device packages have terminals called "pins" for insertion into holes in a printed circuit board (PCB). Other types of device packages have terminals called "leads" for attachment to flat metal contact regions on an exposed surface of a PCB. Newer ball grid array ("BGA") device packages described below have solder balls for attachment to flat metal pads on an exposed surface of a PCB.

As integrated circuit fabrication technology improves, manufacturers are able to integrate more and more functions onto single silicon substrates. As the number of functions on a single integrated circuit increases, the number of signal lines which need to be connected to external devices also increase. The corresponding number of required I/O pads and device package terminals increase as well, as do the complexities and costs of the device packages. Constraints of high-volume PCB assembly operations place lower limits on the physical dimensions of device packages and distances between device package terminals. As a result, the areas of peripheral-terminal device packages having hundreds of terminals are largely proportional to the number of terminals. In addition, the lengths of signal lines from integrated circuit I/O pads to device package terminals increase with the number of terminals, and the high-frequency electrical performance of larger peripheral-terminal device packages suffer as a result.

Controlled collapse chip connection (C4) is a well known method of attaching an integrated circuit directly to a substrate made of, for example, fiberglass-epoxy printed circuit board material or a ceramic material (e.g., aluminum oxide, alumina, $Al_2O_3$, or aluminum nitride, AlN). The C4 attachment method is commonly referred to as the "flip chip" method. The I/O pads of the integrated circuit are typically arranged in a two-dimensional array upon a "frontside" surface of the integrated circuit, and a corresponding set of bonding pads are formed upon an upper surface of the substrate. A solder "bump" is formed upon each of the I/O pads of the integrated circuit. During C4 attachment of the integrated circuit to the substrate, the integrated circuit is inverted and the solder bumps are placed in physical contact with the bonding pads of the substrate. The solder bumps are then heated long enough for the solder to reflow. When the solder cools, the I/O pads of the integrated circuit are electrically and mechanically coupled to the bonding pads of the substrate. After the integrated circuit is attached to the substrate, the region between the integrated circuit and the substrate is filled with an adhesive "underfill" material which encapsulates the C4 connections and provides other mechanical advantages.

Grid array semiconductor device packages have terminals arranged in a two-dimensional array across the underside surface of the device package. As a result, the physical dimensions of grid array device packages having hundreds of terminals are much smaller than their peripheral-terminal counterparts. Such smaller packages are highly desirable in portable device applications such as laptop and palmtop computers and hand-held communications devices such as cellular telephones. In addition, the lengths of signal lines from integrated circuit I/O pads to device package terminals are shorter, thus the high-frequency electrical performances of grid array device packages are typically better than those of corresponding peripheral-terminal device packages. Grid array device packages also allow the continued use of existing PCB assembly equipment developed for peripheral-terminal devices.

The BGA device package is an increasingly popular type of grid array device package. FIG. 1 is a cross-sectional view of a BGA device package 10 in current use. BGA device package 10 is one form of a "flip chip integrated circuit package". BGA device 10 includes an integrated circuit 12 mounted upon an upper surface of a larger package substrate 14. Substrate 14 may be made of, for example, fiberglass-epoxy printed circuit board material or a ceramic material (e.g., aluminum oxide or aluminum nitride). Substrate 14 includes two sets of bonding pads: a first set on an upper surface adjacent to integrated circuit 12 and a second set arranged in a two-dimensional array across the underside surface. The I/O pads of integrated circuit 12 are connected to corresponding members of the first set of bonding pads using the C4 technique described above. Members of the second set of bonding pads function as device package terminals. Solder balls (not shown) attached to members of the second set of bonding pads allow device package 10 to be surface mounted to an ordinary PCB. Substrate 14 includes one or more layers of electrically conductive "traces" (i.e., signal lines) which connect respective members of the first and second sets of bonding pads.

During the C4 mounting of integrated circuit 12 upon substrate 14, solder bumps 16 formed on I/O pads of integrated circuit 12 are placed in physical contact with corresponding members of the first set of bonding pads of substrate 14 and heated long enough for the solder to reflow. When the solder cools, the I/O pads are electrically and mechanically coupled to the corresponding members of the first set of bonding pads. A layer of an adhesive underfill material 18 is then formed in the region between integrated circuit 12 and substrate 14.

The C4 underfill material is typically a thermosetting polymer (e.g., an epoxy resin) which is dispensed in liquid form and becomes substantially rigid (i.e., hardens) during a curing process (e.g., with time and/or elevated temperature). The liquid underfill material is dispensed along one or more sides of integrated circuit 12, and capillary action is relied upon to draw the liquid underfill material into the space between the underside of integrated circuit 12 and the corresponding portion of the upper surface of substrate 14. The underfill material may include suspended particles of a thermally conductive and electrically insulating material (e.g., silica). Once cured, the underfill material essentially interlocks the surfaces of integrated circuit 12 and substrate 14 surrounding the C4 connections, reducing the mechanical forces acting upon the solder bumps during temperature cycling. In addition, the underfill material encapsulates the C4 connections, protecting them from contaminants (e.g., moisture, electrically conductive particles, etc.) As a result, the reliabilities of the solder bump connections are substantially increased.

Following the C4 mounting process, a thermally-conductive heat spreader may be attached to a "backside" surface of integrated circuit 12. The heat spreader conducts heat energy away from integrated circuit 12 during operation. FIG. 2 is a cross-sectional view of a heat spreader 20 attached to the downward-facing backside surface of integrated circuit 12 by an adhesive thermal interface layer 22. Adhesive thermal interface layer 22 may be, for example, a layer of a thermosetting polymer (e.g., an epoxy resin) which is dispensed in liquid form and becomes substantially rigid during a curing process as described above. Adhesive thermal interface layer 22 typically includes particles of a thermally conductive material (e.g., silver, aluminum, boron nitride, etc.).

In order to perform their intended functions, adhesive layers 18 and 22 must remain mechanically locked to the surfaces of their adherents. FIGS. 3–5 will be used to describe several different types of testing performed to provide increased confidence that adhesive layers 18 and 22 will indeed retain this mechanically locked state over time. FIG. 3 is a cross-sectional view of BGA device package 10 of FIG. 1 undergoing tension testing in accordance with a technique in current use. A pull stud 24 is attached to the upward-facing backside surface of integrated circuit 12 by an adhesive layer 26. Adhesive layer 26 has a bonding strength greater than that of the layer of adhesive underfill material 18. Substrate 14 is held in place, and an upward vertical force F, normal to the upper surface of integrated circuit 12, is applied between pull stud 24 and substrate 14. Force F is increased until the layer of adhesive underfill material 18 fails and integrated circuit 12 separates from substrate 14. The maximum tensile force F endured by the layer of adhesive underfill material 18 prior to failure is compared to a predetermined minimum tensile force value. A maximum tensile force F equal to or exceeding the minimum tensile force value indicates long term reliability of the layer of adhesive underfill material 18.

FIG. 4 is a cross-sectional view of BGA device package 10 of FIG. 1 undergoing "peel" testing in accordance with a current technique. Substrate 14 is again held in place, and the beveled edge of a chisel blade 28 is brought into contact with the layer of adhesive underfill material 18. A lateral force F is applied along chisel blade 28 as shown in FIG. 4. Force F tends to cause the layer of adhesive underfill material 18 to pull up and away (i.e., "peel") from substrate 14. Force F is increased until the layer of adhesive underfill material 18 fails and integrated circuit 12 separates from substrate 14. The maximum "peel" force F endured by the layer of adhesive underfill material 18 prior to failure is compared to a predetermined minimum "peel" force value. A maximum "peel" force F equal to or exceeding the minimum "peel" force value indicates long term reliability of the layer of adhesive underfill material 18.

FIG. 5 is a cross-sectional view of BGA device package 10 of FIG. 1 undergoing "shear" testing in accordance with a current technique. Substrate 14 is again held in place, and a notch in a blade 32 of a "pusher" tool is brought into contact with the upper surface and one side of integrated circuit 12 as shown in FIG. 5. A lateral force F is applied along blade 32. Force F tends to cause the layer of adhesive underfill material 18 to separate from and slide over the upper surface of substrate 14. Force F is increased until the layer of adhesive underfill material 18 fails and integrated circuit 12 separates from substrate 14. The maximum "shear" force F endured by the layer of adhesive underfill material 18 prior to failure is compared to a predetermined minimum "shear" force value. A maximum "shear" force F equal to or exceeding the minimum "shear" force value indicates long term reliability of the layer of adhesive underfill material 18.

Disadvantages with the tension, peel, and shear tests shown in FIGS. 3, 4, and 5, respectively, include the time consuming setup steps required for each separate test. In addition, during the peel test in FIG. 4, a portion of force F transmitted from chisel blade 28 to integrated circuit 12 often results in cracks 30 occurring within the brittle semiconductor substrate material of integrated circuit 12. Similarly, during the shear test in FIG. 5, a portion of force F transmitted from blade 32 of the pusher tool to integrated circuit 12 often results in cracks 34 occurring within integrated circuit 12. Such cracks 30 and 34 cause the results of the test to be unreliable. Consequently, when cracks 30 or 34 occur within integrated circuit 12 during testing, the BGA device package 10 under test must be discarded, and the test must be repeated upon a new BGA device package 10.

It would be beneficial to have a single apparatus and associated method which allow either tension, peel, or shear testing to be performed upon various adhesive layers used to connect members of a flip chip integrated circuit package. Such an apparatus would apply a force between integrated circuit 12 and a second adherent (e.g., substrate 14 or heat spreader 20) such that integrated circuit 12 is not damaged during testing. Eliminating damage to integrated circuit 12 reduces the amount of time required to perform testing on a statistically meaningful number of flip chip integrated circuit packages.

SUMMARY OF THE INVENTION

The problems outlined above are in large part solved by an apparatus and method for testing an adhesive layer formed between an integrated circuit and a plate, wherein the plate may be semiconductor device package substrate or a heat spreader. The apparatus includes a pull stud and a pull arm. The pull stud has an upper portion and a lower portion. The lower portion of the pull stud is attached to a surface of the integrated circuit. Such attachment may be accomplished by forming a layer of an adhesive material between the lower portion of the pull stud and the surface of the integrated circuit. To ensure the adhesive layer under test fails first, the bonding strength of the layer of adhesive material exceeds that of the adhesive layer between the integrated circuit and the plate.

When the plate is a semiconductor device substrate, solder bumps connect I/O pads upon the downward-facing frontside surface of the integrated circuit to bonding pads on the upper surface of the device package substrate. A layer of adhesive underfill material formed between the integrated circuit and the plate (i.e., the device package substrate) encapsulates the solder bumps. In order to test the adhesive underfill layer, the lower portion of the pull stud is attached to the upward-facing backside surface of the integrated circuit.

Alternately, the downward-facing backside surface of the integrated circuit may be attached to the upper surface of the heat spreader by an adhesive thermal interface layer. In order to test the adhesive thermal interface layer, the lower portion of the pull stud is attached to the upward-facing frontside surface of the integrated circuit.

The upper portion of the pull stud has two opposed ends. One of the ends (i.e., a large end) has relatively large dimensions (e.g., width, diameter, radius, or circumference) and cross-sectional area. The other end (i.e., a small end) has relatively small dimensions and cross-sectional area. The small end of the upper portion meets the lower portion of the pull stud. In one embodiment, the upper portion of the pull stud is a tapered cylinder. When the pull stud having a tapered cylindrical upper portion is attached to the surface of the integrated circuit, an axis of the cylinder is normal to the upper surface of the integrated circuit.

The pull arm has two opposed ends and at least one bracket for receiving a force. One of the pull arm ends has a "V"-shaped opening surrounded by a lip. The opening receives the upper portion of the pull stud. When the upper portion of the pull stud is inserted into the opening, the lip contacts and retains the upper portion of the pull stud. The opening has an upper wall, and an upper surface of the pull stud contacts the upper wall when the upper portion of the pull stud is inserted into the opening. The lip is vertically displaced from the upper wall such that the lip contacts the upper portion of the pull stud a spaced distance from where the upper surface of the pull stud contacts the upper wall of the opening. In this way, the pull stud and the pull arm are substantially mechanically locked together during use of the apparatus.

The apparatus may also include a holder for holding the plate in place during use. The holder may include an opening dimensioned to receive the plate.

A method for testing the adhesive layer formed between the integrated circuit and the plate employs the apparatus described above. The lower portion of the pull stud is attached to the surface of the integrated circuit opposite the plate. The plate is inserted into the opening of the holder. The upper portion of the pull stud is engaged in the pull arm opening such that the pull stud and the pull arm are substantially mechanically locked together. A force is applied between the bracket and the plate such that the adhesive layer between the integrated circuit and the plate is subjected to the force. The magnitude of the force may be increased until the adhesive layer fails, and the maximum amount of force applied prior to failure of the adhesive layer may be measured.

BRIEF DESCRIPTION OF THE DRAWINGS

Other objects and advantages of the invention will become apparent upon reading the following detailed description and upon reference to the accompanying drawings in which.

Figure 1:
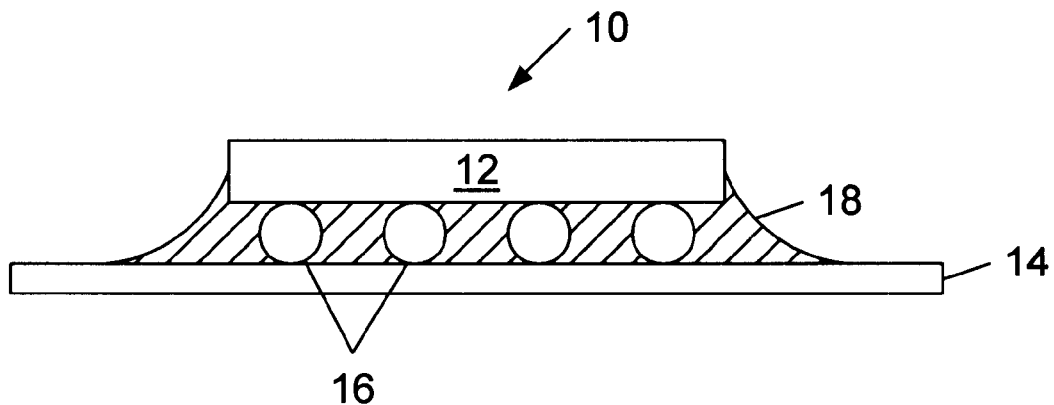
FIG. 1 is a cross-sectional view of a BGA device package in current use, wherein the BGA device package includes an integrated circuit mounted upon an upper surface of a larger package substrate.
Figure 2:
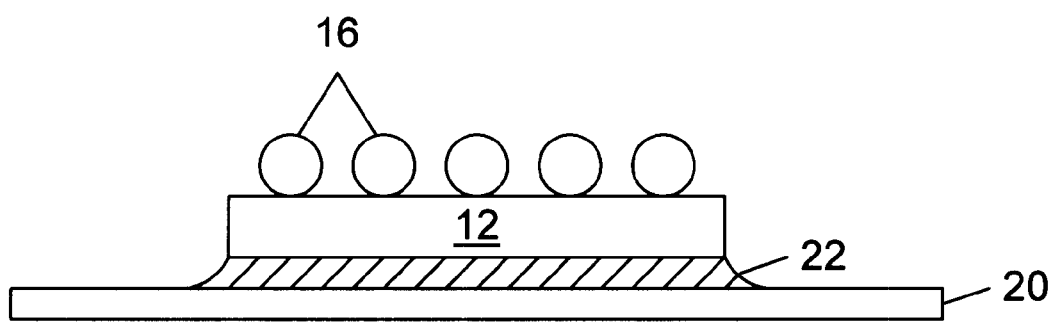
FIG. 2 is a cross-sectional view of a heat spreader attached to a downward-facing backside surface of an integrated circuit by an adhesive thermal interface layer.
Figure 3:
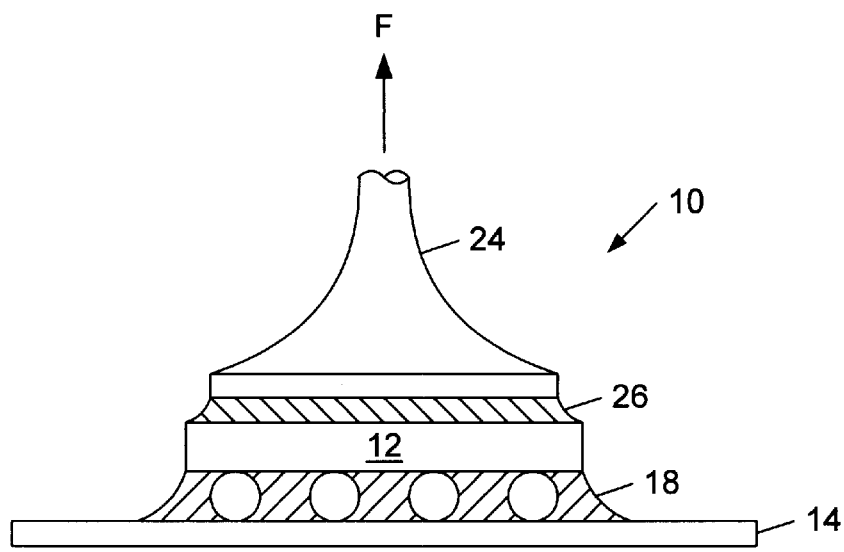
FIG. 3 is a cross-sectional view of the BGA device package of FIG. 1 undergoing tension testing in accordance with a technique in current use.
Figure 4:
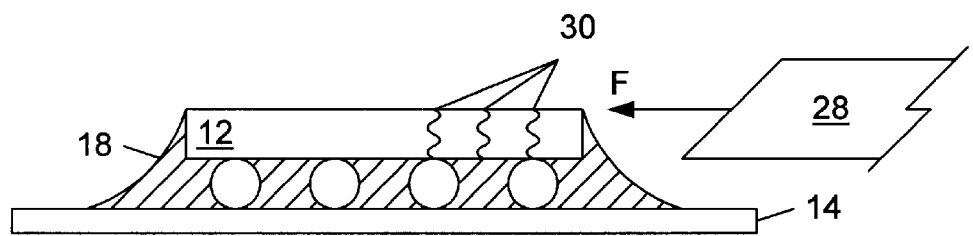
FIG. 4 is a cross-sectional view of the BGA device package of FIG. 1 undergoing "peel" testing in accordance with a current technique.
Figure 5:
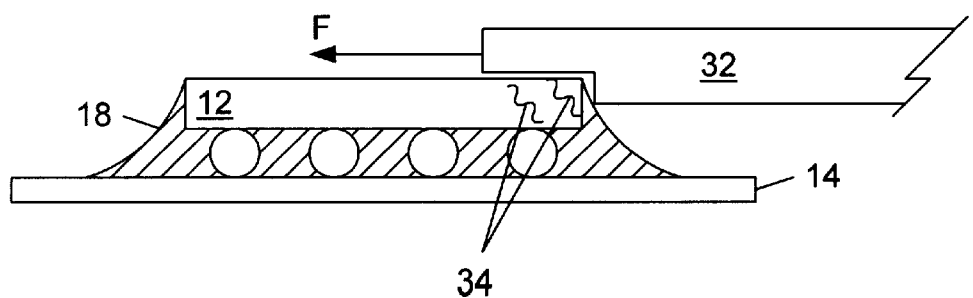
FIG. 5 is a cross-sectional view of BGA device package 10 of FIG. 1 undergoing "shear" testing in accordance with a current technique.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 6:
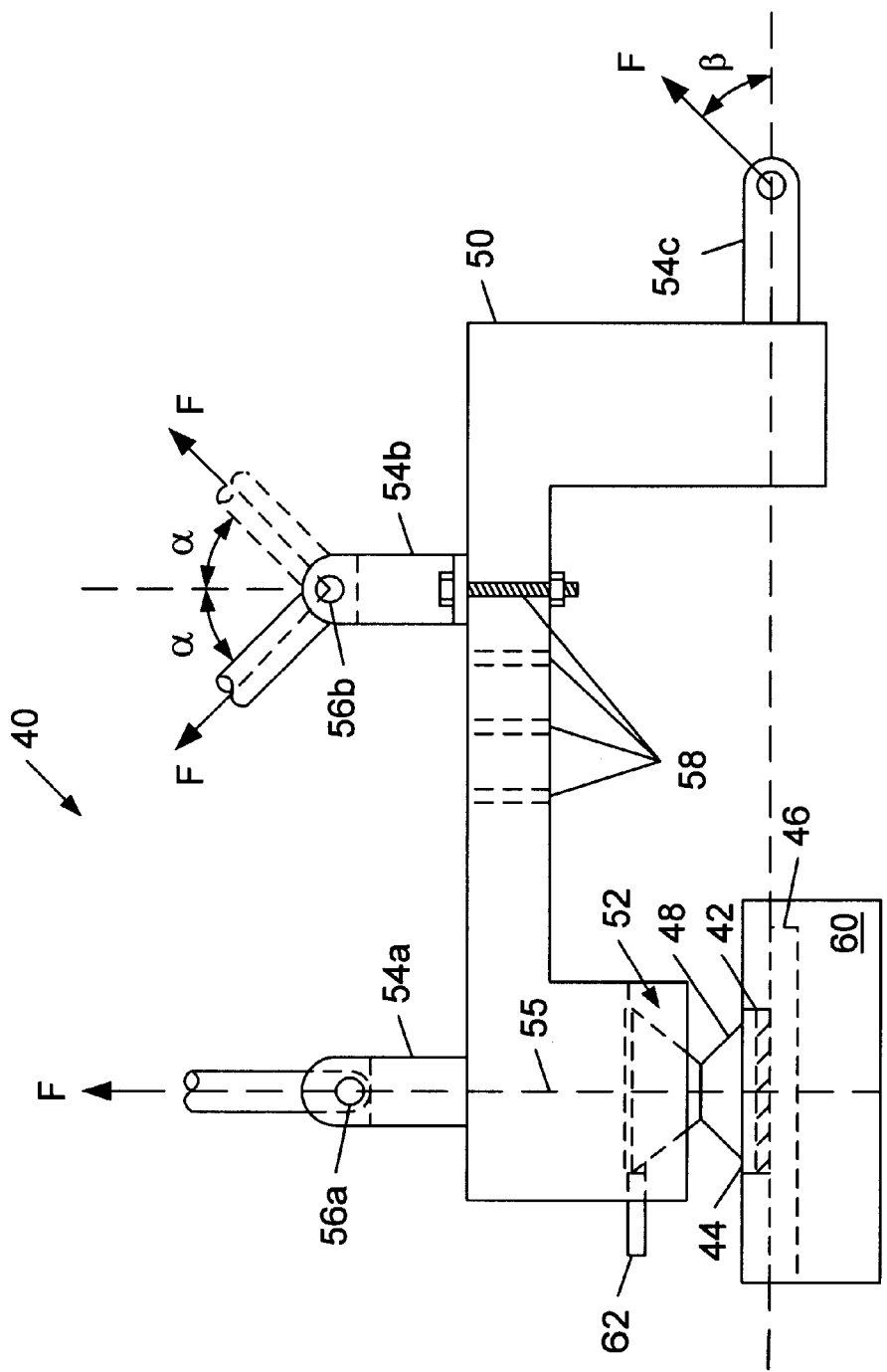
FIG. 6 is side elevation view of one embodiment of an apparatus for testing the mechanical properties of an adhesive layer formed between an integrated circuit and a larger plate, wherein the plate may be a package substrate or a heat spreader, and wherein the apparatus includes a pull stud and a pull arm.

FIG. 6 is side elevation view of one embodiment of an apparatus 40 for testing the mechanical properties of an adhesive layer 42 formed between an integrated circuit 44 and a larger plate 46. Plate 46 may be, for example, a semiconductor device package substrate such as substrate 14 described above. In this case, adhesive layer 42 may be a layer of an adhesive underfill material which encapsulates solder bump connections formed between I/O pads of integrated circuit 44 and a set of bonding pads on the upper surface of device package substrate 14 as described above. Alternately, plate 46 may be a thermally conductive heat spreader such as heat spreader 20 described above. In this case, adhesive layer 42 may be a layer of a thermosetting polymer (e.g., an epoxy resin) which includes particles of a thermally conductive material as described above.

Apparatus 40 includes a pull stud 48 and a pull arm 50. Pull stud 48 has an upper portion and a lower portion. Both the upper and lower portions have two opposed ends, one with relatively large dimensions and cross sectional area (i.e., a large end), and the other having relatively small dimensions and cross sectional area (i.e., a small end). The small ends of the upper and lower portions meet at a waist of pull stud 48. The cross sectional area of pull stud 48 is thus smallest at the waist. During use of apparatus 40, the lower portion of pull stud 48 is attached to integrated circuit 44, and plate 46 is held in place. Pull arm 50 has two opposed ends. The upper portion of pull stud 48 is engaged within an opening 52 in one end (i.e., a first end) of pull arm 50.

One or more brackets 54a–c may be attached to pull arm 50 for applying a force F between pull arm 50 and plate 46 during testing. A first bracket 54a is used to conduct tension testing of adhesive layer 42. Bracket 54a is attached to an upper surface of pull arm 50. Bracket 54a is positioned along the upper surface of pull arm 50 such that when pull stud 48 is engaged within opening 52, bracket 54a is centered on a vertical line 55 passing through the center of integrated circuit 44 and normal to substantially planar major surfaces of adhesive layer 42. When a force F is applied between bracket 54a and plate 46, shear forces within adhesive layer 42 are minimized, and adhesive layer 42 is substantially in tension.

Bracket 54a includes a hinged attachment point 56a. Hinged attachment point 56a helps reduce unwanted torsional or twisting forces which may be transmitted to adhesive layer 42 during use.

A second bracket 54b is used to conduct peel testing of adhesive layer 42. Bracket 54b is also attached to the upper surface of pull arm 50, and is preferably moveably attached to the upper surface of pull arm 50. In the embodiment of FIG. 6, one of several holes 58 extending between the upper surface of pull arm 50 and a lower surface of pull arm 50 may be used to secure bracket 54b in place. Bracket 54b is positioned such that when pull stud 48 is engaged within opening 52, bracket 54b is not centered on the vertical line 55. That is, bracket 54b is positioned a lateral distance from the vertical line 55. As a result, when a force F is applied between bracket 54b and plate 46, substantial tension and shear forces are created within adhesive layer 42. By varying an angle α at which force F is applied with respect to a vertical line normal to the upper surface of pull arm 50 and extending through bracket 54b, various magnitudes of tension and shear forces may be created within adhesive layer 42.

Bracket 54b includes a hinged attachment point 56b. Hinged attachment point 56b helps reduce unwanted torsional or twisting forces which may be transmitted to adhesive layer 42 during use.

A third bracket 54c is used to conduct shear testing of adhesive layer 42. Bracket 54c is attached to the end of pull arm 50 opposite the end with opening 52 (i.e., the second end of pull arm 50). Bracket 54c is centered on a horizontal line in the plane of an upper surface of plate 46 and extending to the second end of pull arm 50. When a force F is applied between bracket 54c and plate 46 and at an angle β with respect to the horizontal line of 0 degrees, any tensile forces within adhesive layer 42 are minimized, and shear forces exceed all other forces within adhesive layer 42. By varying angle β, various magnitudes of tension and shear forces may be created within adhesive layer 42.

Pull arm 50 preferably also includes a knockout pin 62 adjacent to opening 52 as shown in FIG. 6. During testing, the force applied between pull arm 50 and plate 46 often causes the upper portion of pull stud 48 to be wedged or jammed into opening 52. Following testing, tapping an exposed end of knockout pin 62 protruding from pull arm 50 serves to release the upper portion of pull stud 48 from opening 52.

Apparatus 40 may also include a holder 60 for holding plate 46 in place during testing. Holder 60 may be, for example, attached to a fixed object such as an upper surface of a work bench.

Figure 7A:
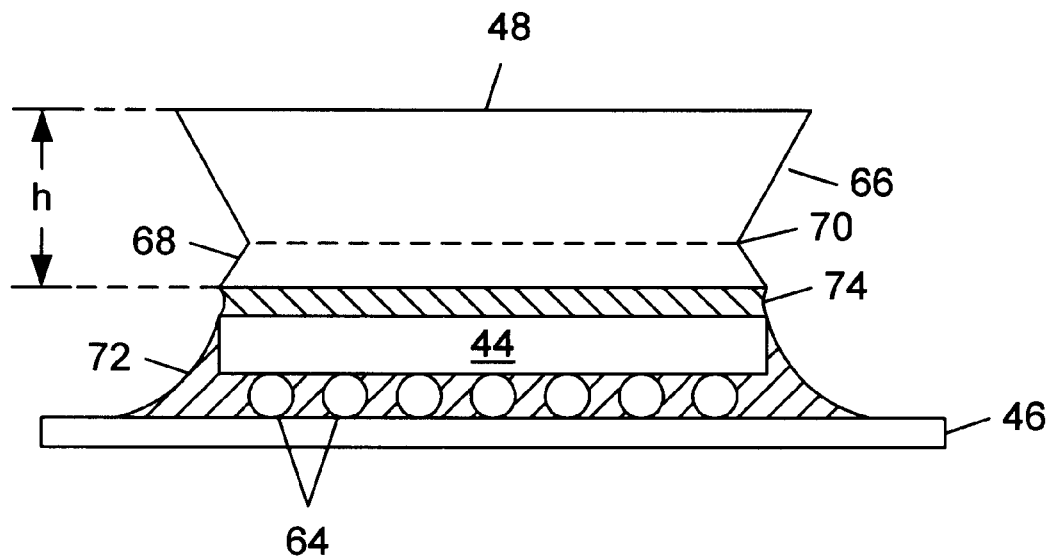
FIG. 7a is a cross-sectional view of the pull stud mounted upon an upward-facing backside surface of the integrated circuit.

FIG. 7a is a cross-sectional view of pull stud 48 mounted upon an upward-facing backside surface of integrated circuit 44. As described above, pull stud 48 has an upper portion (labeled 66) and a lower portion (labeled 68). Both upper portion 66 and lower portion 68 have large ends and small ends. The small ends of upper portion 66 and lower portion 68 meet at a waist 70 of pull stud 48. The cross sectional area of pull stud 48 is thus smallest at waist 70. A height h of pull stud 48 is preferably about 0.25 in.

In FIG. 7a, plate 46 may be a semiconductor device package substrate, and solder bumps 64 connect I/O pads formed upon the downward-facing frontside surface of integrated circuit 44 to a set of bonding pads on the upper surface of the package substrate. An adhesive underfill layer 72, encapsulating solder bumps 64 and mechanically coupling the downward-facing frontside surface of integrated circuit 44 to the adjacent portion of the upper surface of plate (i.e., substrate) 46, is the adhesive layer under test.

Adhesive underfill layer 72 may be, for example, an epoxy compound including suspended particles of a thermally conductive and electrically insulating material (e.g., silica). An exemplary material for adhesive underfill layer 72 is Dexter HYSOL® No. 4527, a silica-filled epoxy (Dexter Electronic Materials, Industry, Calif.).

Lower portion 68 of pull stud 48 may be attached to the upward-facing backside surface of integrated circuit 44 by an adhesive layer 74. Adhesive layer 74 has a bonding strength greater than adhesive underfill layer 72 such that adhesive underfill layer 72 will fail before adhesive layer 74 when a force is applied between pull stud 48 and plate (i.e., substrate) 46. Adhesive layer 72 may be a layer of a thermosetting polymer (e.g., an epoxy resin) which is dispensed in liquid form and becomes substantially rigid during a curing process.

A suitable material for adhesive layer 74 is 5 Minute® Epoxy Gel, product number 14240, made by ITW Devcon, Danvers, Mass. The two-part epoxy adhesive may be mixed per the manufacturer's instructions, applied between lower portion 68 of pull stud 48 and integrated circuit 44, then cured at a temperature of between 80° C. and 150° C. for 45 to 90 minutes.

Figure 7B:
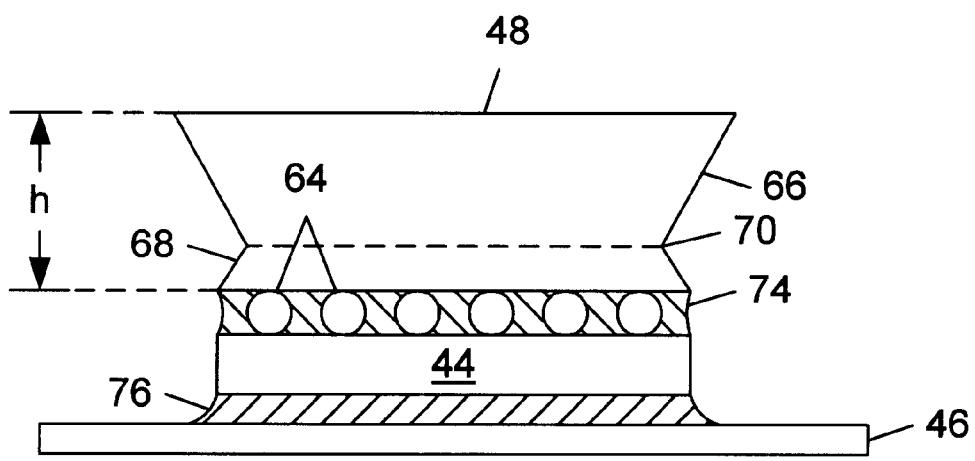
FIG. 7b is a cross-sectional view of the pull stud mounted upon an upward-facing frontside surface of the integrated circuit.

FIG. 7b is a cross-sectional view of pull stud 48 mounted upon the upward-facing frontside surface of integrated circuit 44. Lower portion 68 of pull stud 48 may be attached to the upward-facing backside surface of integrated circuit 44 by adhesive layer 74. In this case, however, adhesive layer 74 is formed around solder bumps 64 on the upward-facing frontside surface of integrated circuit 44. The downward-facing backside surface of integrated circuit 44 is attached to an adjacent portion of an upward-facing surface of plate 46 by an adhesive thermal interface layer 76. Plate 46 may be a thermally-conductive heat spreader, and adhesive thermal interface layer 76 may be a layer of a thermosetting polymer (e.g., an epoxy resin) including particles of a thermally conductive material (e.g., silver, aluminum, boron nitride, etc.). In FIG. 7b, adhesive thermal interface layer 76 attaching the downward-facing backside surface of integrated circuit 44 to the adjacent portion of the upward-facing surface of plate (i.e., heat spreader) 46 is the adhesive layer under test. Adhesive layer 74 attaching pull stud 48 to integrated circuit 44 has a bonding strength greater than adhesive thermal interface layer 76 such that adhesive thermal interface layer 76 will fail before adhesive layer 74 when a force is applied between pull stud 48 and plate (i.e., heat spreader) 46. Again, a height h of pull stud 48 is preferably about 0.25 in.

A bottom end of pull stud 48 is also the large end of lower portion 68, and is adapted for attachment to integrated circuit 44. The large end of lower portion 68 is preferably dimensioned to substantially cover one of two opposing major surfaces of integrated circuit 44. It is desirable that the cross sectional area of an attachment region existing between the lower end of pull stud 48 and an adjacent major surface of integrated circuit 44 be as large as possible. A force applied to pull stud 48 is transferred to integrated circuit 44 through the attachment region. When the attachment region is as large as possible, the force is more evenly distributed across the surface of integrated circuit 44, and a concentration of force is avoided which may crack or break the brittle semiconductor substrate material of integrated circuit 44.

Figure 8A:
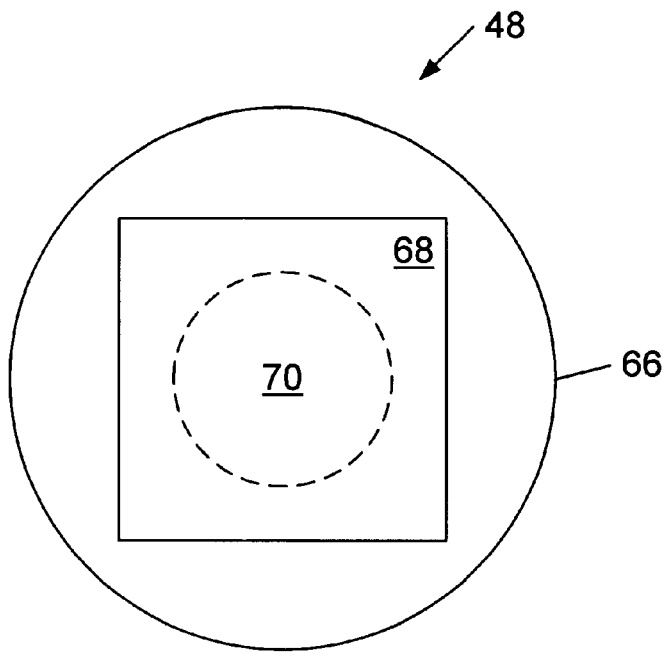
FIG. 8a is a bottom plan view of one embodiment of the pull stud, wherein the pull stud has an upper portion and a lower portion, and wherein the upper portion of the pull stud is a tapered cylinder, and wherein the lower portion has a small end and a large end, and wherein the small end of the lower portion has a circular cross section, and wherein the large end of the lower portion has a substantially rectangular cross section.

FIG. 8a is a bottom plan view of one embodiment of pull stud 48. In FIG. 8a, upper portion 66 of pull stud 48 is a tapered cylinder having a circular cross section and tapering from a large end to a small end. Lower portion 68 of pull stud 48 also has a large end and a small end. The small end of lower portion 68 meets the small end of upper section 66 at waist 70, and has a circular cross section. In the embodiment of FIG. 8a, the large end of lower portion 68 has a substantially rectangular cross section. The dimensions of the large end of lower portion 68 may be made equal to the dimensions of the rectangular major surfaces of integrated circuit 44, advantageously providing the largest possible attachment region between pull stud 48 and integrated circuit 44.

Figure 8B:
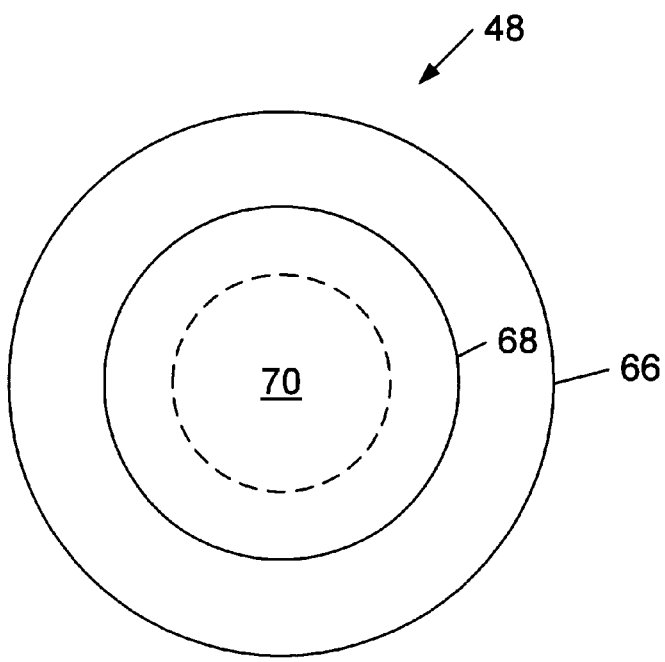
FIG. 8b is a bottom plan view of an alternate embodiment of the pull stud, wherein both the upper and lower portions are tapered cylinders.

FIG. 8b is a bottom plan view of an alternate embodiment of pull stud 48. As in FIG. 8a, upper portion 66 of pull stud 48 is a tapered cylinder having a circular cross section and tapering from a large end to a small end. In FIG. 8b, lower portion 68 is also a tapered cylinder having a circular cross section and tapering from a large end to a small end. As before, the small end of lower portion 68 meets the small end of upper section 66 at waist 70. In the embodiment of FIG. 8b, the large end of lower portion 68 has a circular cross section, and is preferably dimensioned to substantially cover a major surface of integrated circuit 44.

Figure 9:
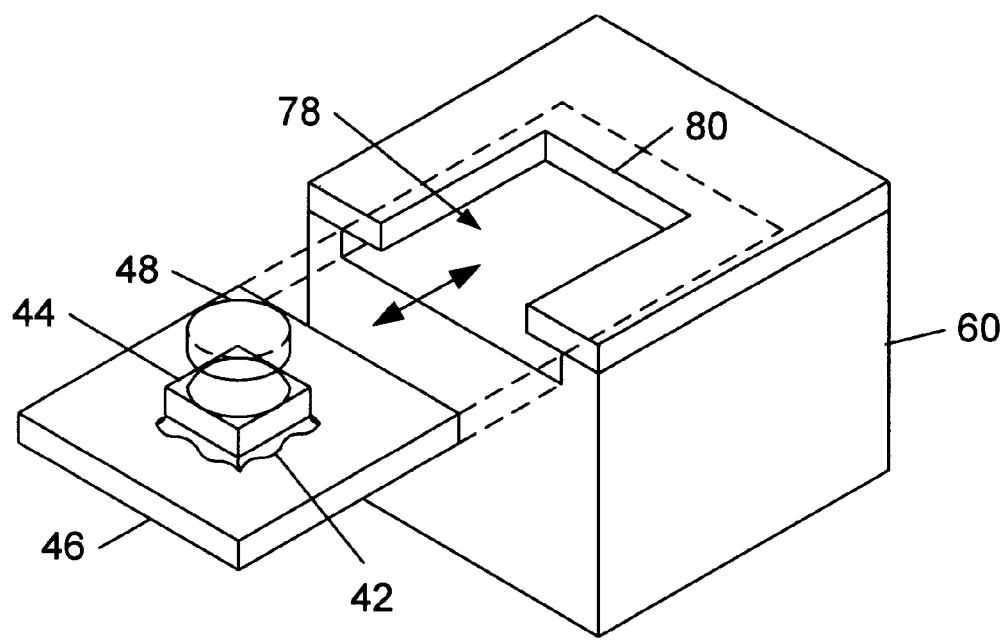
FIG. 9 is an isometric view of an optional holder for holding the plate in place during testing.

FIG. 9 is an isometric view of holder 60. Holder 60 has an opening 78 dimensioned to receive plate 46. As described above, holder 60 holds plate 46 in place during testing. Holder 60 also prevents plate 46 from twisting, warping, or rotating during testing. Pull stud 48 is attached to an upward-facing major surface of integrated circuit 44. The opposed downward-facing major surface of integrated circuit 44 is attached to plate 46 by adhesive layer 42, the adhesive layer under test. Plate 46 may be a semiconductor device package substrate, in which case adhesive layer 42 is adhesive underfill layer 72. (See FIG. 7a). Alternately, plate 46 may be a thermally conductive heat spreader, in which case adhesive layer 42 is adhesive thermal interface layer 76. (See FIG. 7b). An upper surface of holder 60 has a cutout portion which allows access to pull stud 48 when plate 46 is inserted into opening 78. A lip 80 in the upper surface of holder 60 surrounds integrated circuit 44 on three sides, and serves to keep plate 46 from moving in an upward direction during testing.

Figure 10A:
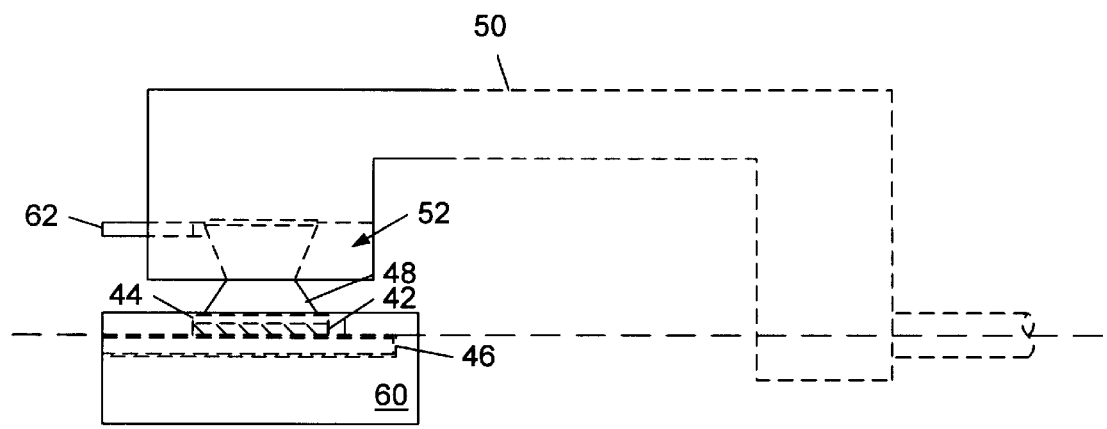
FIG. 10a is a side elevation view of the embodiment of the apparatus as shown in FIG. 6 highlighting an end of the pull arm in which a "V"-shaped opening is located, wherein a lip surrounds the opening, and wherein the opening engages the upper portion of the pull stud during use.
Figure 10B:
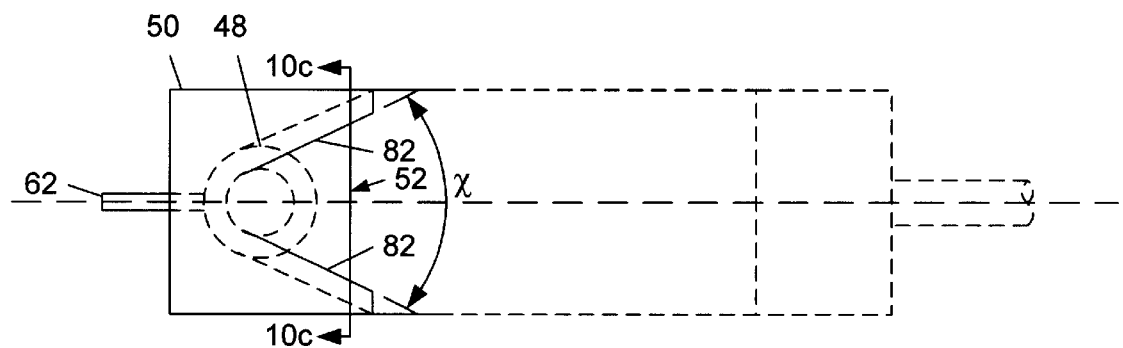
FIG. 10b is a bottom plan view of the pull arm of FIG. 10a further illustrating the opening and the pull stud engaged therein.
Figure 10C:
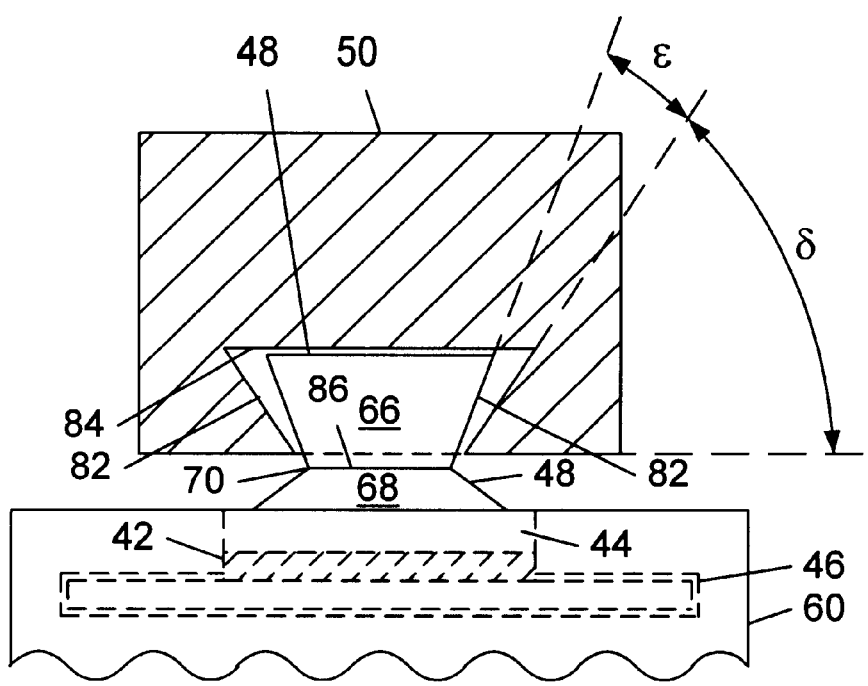
FIG. 10c is a cross sectional view of the pull arm of FIG. 10a further illustrating the opening and the pull stud engaged therein as indicated in FIG. 10b.

FIGS. 10a–c will now be used to describe opening 52 in pull arm 50. FIG. 10a is a side elevation view of the embodiment of apparatus 40 shown in FIG. 6 highlighting the end of pull arm 50 in which opening 52 is located. FIG. 10b is a bottom plan view of pull arm 50 further illustrating opening 52 and pull stud 48 engaged therein. Opening 52 is a "V"-shaped, tapered dovetail slot adapted to engage upper portion 66 of pull stud 48. (See FIGS. 7a–b). Sides 82 of opening 52 are tapered to conform to and engage the tapered sides of conical upper portion 66. Sides 82 contact and retain the upper portion of the pull stud during use. An angle X formed between sides 82 of opening 52 is preferably between 5 and 10 degrees.

FIG. 10c is a cross sectional view of pull arm 50 and the engaged pull stud 48 as indicated in FIG. 10b. An angle δ formed between a bottom surface of pull arm 50 and a wall of each side 82 as shown in FIG. 10c is preferably between 45 and 60 degrees. An angle ε formed between the wall of each side 82 and the sides of conical upper portion 66 of pull stud 48 is preferably between 1 and 3 degrees.

When pull stud 48 is engaged within opening 52 of pull arm 50, an upper surface of pull stud 48 contacts an upper wall 84 of opening 52, forming a first contact region between pull arm 50 and pull stud 48. The lowermost portions of sides 82 effectively form a lip surrounding opening 52. A second contact region is formed along the bottom surface of pull arm 50 where the lip formed by the lowermost portions of sides 82 contacts pull stud 48 along a horizontal line 86 just above waist 70 of pull stud 48 as shown in FIG. 10c. The lip serves to retain upper portion 66 of pull stud 48 during testing. The distance existing between the first and second contact regions helps ensure pull stud 48 and pull arm 50 are substantially mechanically locked together when pull stud 48 is engaged within opening 52 of pull arm 50. Being substantially mechanically locked together, a force applied to pull arm 50 is transferred through pull stud 48 and integrated circuit 44 to adhesive layer 42 under test.

A method for testing the adhesive layer formed between the integrated circuit and the plate employs apparatus 40. Lower portion 68 of pull stud 48 is attached to the upper surface of integrated circuit 44. Attachment of pull stud 48 to integrated circuit 44 may be accomplished using adhesive layer 74 as described above. Plate 46 is inserted into opening 78 of holder 60. Upper portion 66 of pull stud 48 is engaged in opening 52 of pull arm 50 such that pull stud 48 and pull arm 50 are substantially mechanically locked together. A force is applied between bracket 54a (tension testing), 54b (peel testing), or 54c (shear testing) of pull arm 50 and plate 46 such that adhesive layer 42 between integrated circuit 44 and plate 46 is subjected to the force. The magnitude of the force may be increased until adhesive layer 42 fails. The maximum amount of force applied between pull arm 50 and plate 46 prior to failure of adhesive layer 42 may be measured.

It will be appreciated to those skilled in the art having the benefit of this disclosure that this invention is believed to be an apparatus and method for testing the mechanical properties of an adhesive layer formed between an integrated circuit and plate, wherein the plate may be a semiconductor device package substrate or a heat spreader. Furthermore, it is also to be understood that the form of the invention shown and described is to be taken as exemplary, presently preferred embodiments. Various modifications and changes may be made without departing from the spirit and scope of the invention as set forth in the claims. It is intended that the following claims be interpreted to embrace all such modifications and changes.

What is claimed is:

1. A method for testing an adhesive layer formed between an integrated circuit and a plate, comprising:

providing:
- a pull stud having an upper portion and a lower portion, wherein the lower portion is adapted for attaching to a surface of the integrated circuit;
- a pull arm comprising:
  - two opposed ends, wherein one of the two ends has a "V"-shaped opening surrounded by a lip, and wherein the opening is adapted to receive the upper portion of the pull stud, and wherein the lip contacts and retains the upper portion of the pull stud during use; and
  - at least one bracket for receiving a force; and
- a holder for holding the plate in place during use, wherein the holder has an opening dimensioned to receive the plate;

attaching the lower portion of the pull stud to the surface of the integrated circuit;

inserting the plate into the opening of the holder;

engaging the upper portion of the pull stud in the opening of the pull arm such that the pull stud and the pull arm are substantially mechanically locked together; and applying a force between the bracket and the plate such that the adhesive layer between the integrated circuit and the plate is subjected to said force.

2. The method as recited in claim 1, wherein the attaching step comprises forming a layer of adhesive material between the lower portion of the pull stud and the surface of the integrated circuit, wherein the bonding strength of the layer of adhesive material exceeds that of the adhesive layer between the integrated circuit and the plate.

3. The method as recited in claim 1, further comprising:
- increasing the magnitude of the force until the adhesive layer fails, and
- measuring the maximum amount of force applied prior to failure of the adhesive layer.

* * * * *